United States Patent
Lee et al.

(10) Patent No.: US 11,148,127 B2
(45) Date of Patent: Oct. 19, 2021

(54) BISPHOSPHINE LIGAND COMPOUND, CHROMIUM COMPOUND, ETHYLENE OLIGOMERIZATION CATALYST SYSTEM, AND ETHYLENE OLIGOMER PREPARATION METHOD

(71) Applicants: AJOU UNIVERSITY INDUSTRY-ACADEMIC COOPERATION FOUNDATION, Suwon-si (KR); S-PRECIOUS CATALYSTS INC., Gyeongju-si (KR)

(72) Inventors: Bun Yeoul Lee, Suwon-si (KR); Tae Hee Kim, Bucheon-si (KR); Hee Soo Park, Seoul (KR); Jun Won Baek, Incheon (KR); Su Jin Gwon, Seongnam-si (KR); Sung Dong Kim, Seoul (KR)

(73) Assignees: AJOU UNIVERSITY INDUSTRY-ACADEMIC COOPERATION FOUNDATION, Suwon-si (KR); S-PRECIOUS CATALYSTS INC., Gyeongju-si (KR)

(*) Notice: Subject to any disclaimer, the term of this patent is extended or adjusted under 35 U.S.C. 154(b) by 0 days.

(21) Appl. No.: 16/972,117

(22) PCT Filed: Jun. 3, 2019

(86) PCT No.: PCT/KR2019/006678
§ 371 (c)(1),
(2) Date: Dec. 4, 2020

(87) PCT Pub. No.: WO2019/235799
PCT Pub. Date: Dec. 12, 2019

(65) Prior Publication Data
US 2021/0229084 A1 Jul. 29, 2021

(30) Foreign Application Priority Data

Jun. 7, 2018 (KR) .................. 10-2018-0065519
May 9, 2019 (KR) .................. 10-2019-0054548

(51) Int. Cl.
*B01J 31/24* (2006.01)
*B01J 31/14* (2006.01)
(Continued)

(52) U.S. Cl.
CPC ......... *B01J 31/2438* (2013.01); *B01J 31/143* (2013.01); *C07C 2/36* (2013.01);
(Continued)

(58) Field of Classification Search
CPC .. B01J 31/2438; B01J 31/143; B01J 2531/62; B01J 2231/20; C07F 11/00; C07C 2/36; C07C 2531/14; C07C 2531/24
See application file for complete search history.

(56) References Cited

U.S. PATENT DOCUMENTS

| 7,511,183 B2 | 3/2009 | Blann et al. |
| 2018/0086860 A1* | 3/2018 | Sa .............................. C07C 2/08 |

FOREIGN PATENT DOCUMENTS

| KR | 10-2006-0002742 A | 1/2006 |
| KR | 10-2015-0006474 A | 1/2015 |

(Continued)

OTHER PUBLICATIONS

Martin J. Hanton, et al, "Bis(imino)pyridine Complexes of the First-Row Transition Metals: Alternative Methods of Activation", Organometallics 2008, 27, 5712-5716, 5 pages.
(Continued)

*Primary Examiner* — Ali Z Fadhel
(74) *Attorney, Agent, or Firm* — Sughrue Mion, PLLC

(57) ABSTRACT

The present invention relates to a bisphosphine ligand compound, a chromium compound prepared using same, an
(Continued)

ethylene oligomerization catalyst system containing the chromium compound, and an ethylene oligomer preparing method, wherein the bisphosphine ligand compound is suitable for mass production and commercial processes, allows extremely high activity to be compatible with excellent economical benefit, and increases selectivity for ethylene oligomerization reaction, thereby being able to be used to manufacture 1-hexene and/or 1-octene at high yield.

10 Claims, 2 Drawing Sheets

(51) Int. Cl.
    *C07C 2/36*     (2006.01)
    *C07F 11/00*     (2006.01)

(52) U.S. Cl.
    CPC ........... *C07F 11/00* (2013.01); *B01J 2231/20* (2013.01); *B01J 2531/62* (2013.01); *C07C 2531/14* (2013.01); *C07C 2531/24* (2013.01)

(56) References Cited

FOREIGN PATENT DOCUMENTS

| | | |
|---|---|---|
| KR | 10-2016-0099449 A | 8/2016 |
| KR | 10-2016-0146482 A | 12/2016 |
| KR | 10-1764165 B1 | 7/2017 |
| KR | 10-1766224 B1 | 8/2017 |

OTHER PUBLICATIONS

Tom E. Stennett, et al., "Avoiding MAO: Alternative Activation Methods in Selective Ethylene Oligomerization", Organometallics, 2012, 6960-6965, 6 pages.

David S. McGuinness, et al., "Ethylene Tri- and Tetramerization with Borate Cocatalysts: Effects on Activity, Selectivity, and Catalyst Degradation Pathways", Organometallics 2007, 26, 1108-1111, 4 pages.

David S. McGuinness, et al., "Cocatalyst Influence in Selective Oligomerization: Effect on Activity, Catalyst Stability, and 1-Hexene/1-Octene Selectivity in the Ethylene Trimerization and Tetramerization Reaction", Organometallics 2007, 26, 2561-2569, 9 pages.

Adam J. Rucklidge, et al., "Ethylene Tetramerization with Cationic Chromium(I) Complexes", Organometallics 2007, 26, 2782-2787, 6 pages.

Eun Ho Kim, et al., "Methylaluminoxane-Free Chromium Catalytic System for Ethylene Tetramerization", ACS Omega, 2017, p. 765-773, 9 pages.

Junpeng He, et al, "A PCP Pincer Ligand for Coordination Polymers with Versatile Chemical Reactivity: Selective Activation of CO2 Gas over CO Gas in the Solid State", Angewandte Chemie International Edition 2016, 55, 12351, 1-6, 6 pages.

Tae Hee Kim, et al., "MAO-free and extremely active catalytic system for ethylene tetramerization", Applied Organometallic Chemistry, vol. 33, e4829, 1-13, 2019, 13 pages.

Peter Jutzi, et al., "Synthesis, Crystal Structure, and Application of the Oxonium Acid [H(OEt2)2]+[B(C6F5)4]-", Organometallics 2000, 19, 1442-1444, 3 pages.

International search report for PCT/KR2019/006678 dated Sep. 6, 2019.

* cited by examiner

[FIG. 1]
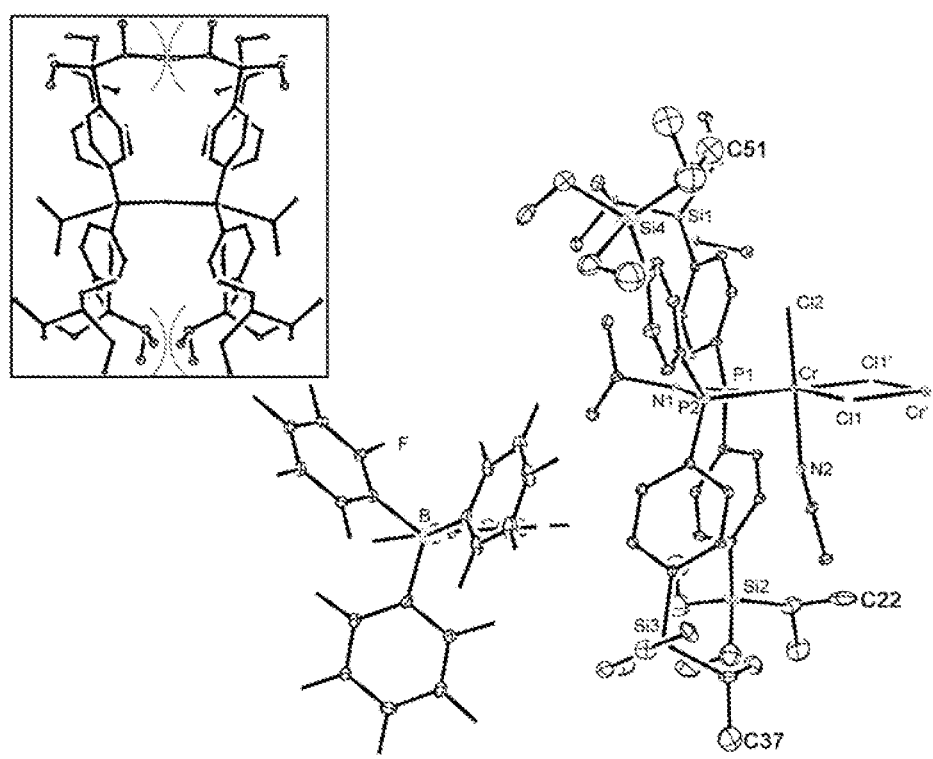

[FIG. 2]
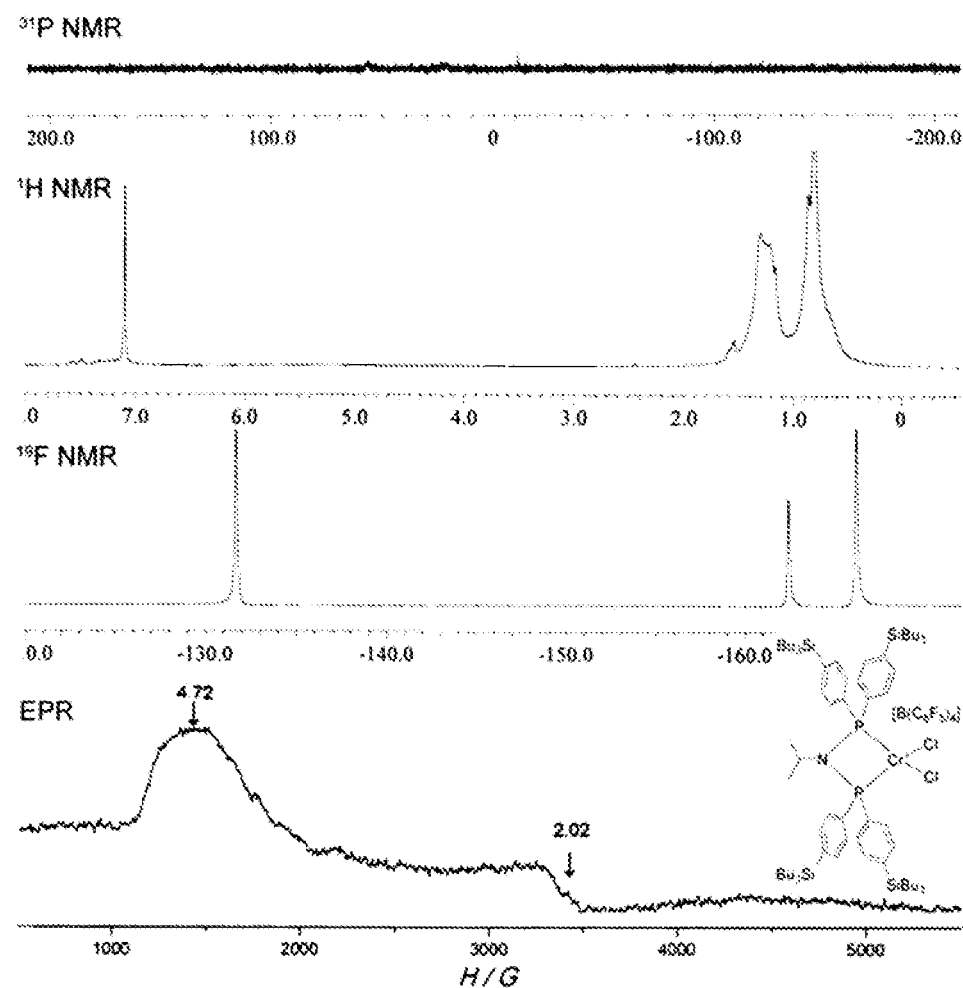

BISPHOSPHINE LIGAND COMPOUND, CHROMIUM COMPOUND, ETHYLENE OLIGOMERIZATION CATALYST SYSTEM, AND ETHYLENE OLIGOMER PREPARATION METHOD

CROSS-REFERENCE TO RELATED APPLICATIONS

This application is a National Stage of International Application No. PCT/KR2019/006678 filed Jun. 3, 2019, which claims priority under U.S.C. § 119(a) to Korean Patent Application Nos. 10-2018-0065519 filed Jun. 7, 2018 and 10-2019-0054548 filed May 9, 2019.

TECHNICAL FIELD

The present invention relates to a bisphosphine ligand compound, which is suitable for mass production and commercial processes, can ensure compatibility between extremely high activity and excellent economic benefit and can increase selectivity for ethylene oligomerization reaction so as to be used in preparation of 1-hexene and/or 1-octene at high yield; a chromium compound prepared using the same; an ethylene oligomerization catalyst system comprising the chromium compound; and an ethylene oligomer preparation method using the same.

BACKGROUND ART 1-hexene and/or 1-octene are ethylene oligomer compounds, which are used in large amounts as comonomers in polymerization of a polyolefin, such as polyethylene. In recent years, with increasing production of a polyolefin using a homogeneous metallocene catalyst, there is increasing demand for, particularly, 1-hexene and 1-octene among ethylene oligomers.

In the related art, various 1-alkenes having about 4 to about 30 carbon atoms were prepared through oligomerization of ethylene by a shell higher olefin process (SHOP) based on a nickel catalyst and 1-hexene and/or 1-octene may be isolated therefrom. Thereafter, a catalyst system capable preparing 1-hexene or 1-hexene and 1-octene at high yield through improvement in selectivity for ethylene oligomerization reaction was invented.

By way of example, a catalyst system developed by Sassol Limited is composed of $CrCl_3$ or $Cr(acac)_3$ as a chromium (III) compound, $iPrN(PPh_2)_2$ as a bisphosphine ligand, and methylaluminoxane (MAO) or modified-methylaluminoxane (MMAO) as a co-catalyst, and selectively produces 1-octene and 1-hexene (Patent Documents 1 and 2).

However, such a conventional catalyst system has drawbacks, such as requirement for a large amount of expensive MAO or MMAO (Al/Cr=300 to 500) for commercially available activity, a low optimal activity temperature of about 60° C., and a high production rate of undesired polyethylene (PE) byproducts, causing increase in preparation costs and low productivity while obstructing commercialization of the catalyst system (Non-patent Documents 1 and 2).

Specifically, when activity is converted into activity per input amount of MAO or MMAO, the conventional catalyst system has a low commercial advantage due to the use of the large amount of expensive MAO or MMAO. Moreover, the low optimal activity temperature of about 60° C. causes rapid deterioration in efficiency in control of reaction heat through air cooling or water cooling and generates a balloon effect even in the case of generating a small amount of polyethylene byproducts, thereby deteriorating the benefit of mass production.

Although the development of catalyst systems not requiring the use of expensive MAO has been actively carried out, such catalyst systems generally have much lower activities than the catalyst system using MAO and are not suitable for commercial availability (Non-patent Documents 3 to 5).

For these reasons, various attempts have been made to develop a catalyst system that does not employ MAO or MMAO, has a high optimal activity temperature of about 80° C., and can extremely suppress generation of polyethylene byproducts. However, it is very difficult for a conventional technology to realize sufficiently high activity, particularly mass production of such a highly active catalyst, without using MAO or MMAO.

Therefore, there is an increasing need for development of an ethylene oligomerization technology, which can prepare 1-hexene and/or 1-octene at high selectivity and good productivity upon contacting ethylene monomers while ensuring compatibility between high activity and economic feasibility.

PRIOR LITERATURE

Patent Document 1: Korean Patent Laid-open Publication No. 10-2006-0002742
Patent Document 2: U.S. Pat. No. 7,511,183 B2
Non-patent Document 1: Organometallics, 27 (2008) 5712-5716
Non-patent Document 2: Organometallics, 31 (2012) 6960-6965
Non-patent Document 3: Organometallics, 26 (2007) 1108-1111
Non-patent Document 4: Organometallics, 26 (2007) 2561-2569
Non-patent Document 5: Organometallics, 26 (2007) 2782-2787
Non-patent Document 6: ACS Omega, 2 (2017) 765-773
Non-patent Document 7: Angewandte Chemie International Edition 2016, 55, 12351

DISCLOSURE

Technical Problem

It is one aspect of the present invention to provide a bisphosphine ligand compound having advantageous characteristics for preparation of a chromium compound and an ethylene oligomerization catalyst system including the chromium compound.

It is another aspect of the present invention to provide a chromium compound that can ensure remarkable improvement in activity and selectivity for ethylene oligomerization reaction to allow preparation of 1-hexene and/or 1-octene at high yield even without using methylaluminoxane (MAO) or modified-methylaluminoxane (MMAO).

It is a further aspect of the present invention to provide an ethylene oligomerization system that can realize good selectivity for 1-hexene and/or 1-octene in application to ethylene oligomerization reaction and is suitable for mass production by ensuring compatibility between high activity and excellent economic feasibility.

It is yet another aspect of the present invention to provide an ethylene oligomer preparation method, which is suitable for mass production and can ensure compatibility between extremely high activity and excellent economic feasibility while ensuring remarkable improvement in activity and selectivity for ethylene oligomerization reaction to allow preparation of 1-hexene and/or 1-octene at high yield even without using methylaluminoxane (MAO) or modified-methylaluminoxane (MMAO).

The above and other aspects of the present invention will become apparent from the detailed description of the following embodiments.

Technical Solution

One embodiment of the present invention relates to a bisphosphine ligand compound represented by Formula A.

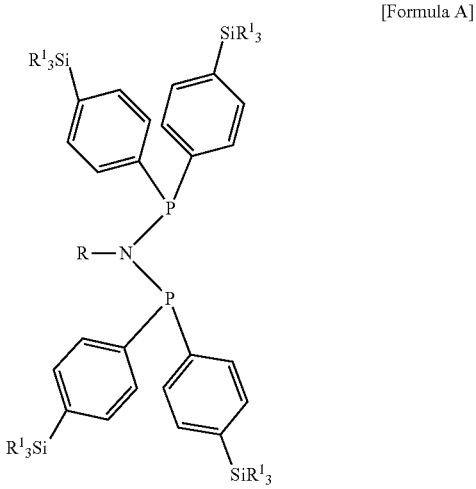

[Formula A]

wherein Formula A, R is a substituted or unsubstituted $C_1$ to $C_{60}$ alkyl group or a substituted or unsubstituted $C_6$ to $C_{60}$ aryl group and $R^1$s are a substituted or unsubstituted $C_1$ to $C_{60}$ alkyl group or a substituted or unsubstituted $C_6$ to $C_{60}$ aryl group.

In Formula A, R may be $[CH_3(CH_2)_d]_2CH$—* (d being an integer of 0 to 20) and $R^1$s may be each independently an ethyl group, an isopropyl group, or an n-butyl group.

Another embodiment relates to a chromium compound represented by Formula 1.

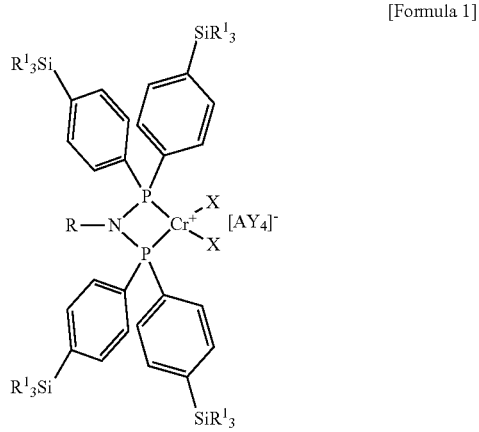

[Formula 1]

wherein Formula 1, R is a substituted or unsubstituted $C_1$ to $C_{60}$ alkyl group or a substituted or unsubstituted $C_6$ to $C_{60}$ aryl group; $R^1$s are a substituted or unsubstituted $C_1$ to $C_{60}$ alkyl group or a substituted or unsubstituted $C_6$ to $C_{60}$ aryl group; Xs are each independently a halogen atom, a $C_2$ to $C_{30}$ carboxylate, acetylacetonate, or a $C_1$ to $C_{30}$ hydrocarbyl group containing or free from at least one selected from among an ether group and an amine group; A is boron or aluminum; and Y is a fluorine-substituted $C_6$ to $C_{20}$ aryl group, a fluorine-substituted $C_6$ to $C_{20}$ aryloxy group, or a fluorine-substituted $C_1$ to $C_{20}$ alkoxy group.

In Formula 1, $[AY_4]^-$ may be $[B(C_6F_5)_4]^-$.

In Formula 1, R may be $[CH_3(CH_2)_d]_2CH$—* (d being an integer of 0 to 20) and $R^1$s may be each independently an ethyl group, an isopropyl group, or an n-butyl group.

In Formula 1, R may be an isopropyl group; $R^1$s may be an n-butyl group; Xs may be Cl; and $[AY_4]^-$ may be $[B(C_6F_5)_4]^-$.

A further embodiment of the present invention relates to an ethylene oligomerization catalyst system including: the chromium compound represented by Formula 1; and an organic aluminum compound represented by Formula 2.

$$(R^2)_3Al \qquad [\text{Formula 2}]$$

wherein Formula 2, $R^2$ is a $C_1$ to $C_{20}$ alkyl group.

In Formula 2, $R^2$ may be an isobutyl group, or an ethyl group.

In the ethylene oligomerization catalyst system, in Formula 1, R may be an isopropyl group; and $R^1$s may be each independently an ethyl group, an isopropyl group, or an n-butyl group; X may be Cl; and $[AY_4]^-$ may be $[B(C_6F_5)_4]^-$.

Yet another embodiment of the present invention relates to an ethylene oligomer preparation method including: selectively preparing 1-hexene and/or 1-octene by bringing the catalyst system into contact with an ethylene monomer.

Advantageous Effects

The present invention provides a bisphosphine ligand compound having advantageous characteristics for preparation of a chromium compound and an ethylene oligomerization catalyst system including the chromium compound.

The present invention provides a chromium compound that can ensure remarkable improvement in activity and selectivity for ethylene oligomerization reaction to allow preparation of 1-hexene and/or 1-octene at high yield even without using methylaluminoxane (MAO) or modified-methylaluminoxane (MMAO).

The present invention provides an ethylene oligomerization system that can realize good selectivity for 1-hexene and/or 1-octene in application to ethylene oligomerization reaction and is suitable for mass production by ensuring compatibility between high activity and excellent economic feasibility.

The present invention provides an ethylene oligomer preparation method, which is suitable for mass production and can ensure compatibility between extremely high activity and excellent economic feasibility while ensuring remarkable improvement in activity and selectivity for ethylene oligomerization reaction to allow preparation of 1-hexene and/or 1-octene at high yield even without using methylaluminoxane (MAO) or modified-methylaluminoxane (MMAO).

DESCRIPTION OF DRAWINGS

FIG. 1 shows a structure of a chromium compound prepared in Example 5, as analyzed by X-ray crystallography.

FIG. 2 shows $^{31}$P NMR spectrum, $^1$H NMR spectrum, $^{19}$F NMR spectrum and EPR spectrum analysis results of a chromium compound prepared in Example 1.

BEST MODE

Herein, unless stated otherwise, symbols, such as H, B, C, N, O, F, P, Cr, Cl, Si, and the like, in the following formulas mean elements represented by the corresponding element symbols.

Herein, unless stated otherwise, '*' in the following formulas means a linking site in a corresponding chemical structure.

Herein, unless stated otherwise, '-' in the following formulas means a bonding site in a corresponding chemical structure.

Herein, in the following formulas, Me means methyl, Et means ethyl, Pr means propyl, iPr means isopropyl, Bu means butyl, Ph means phenyl, acac means acetylacetonate, and THF means tetrahydrofuran.

<Bisphosphine Ligand Compound for Ethylene Oligomerization Reaction>

One embodiment of the present invention relates to a bisphosphine ligand compound represented by Formula A.

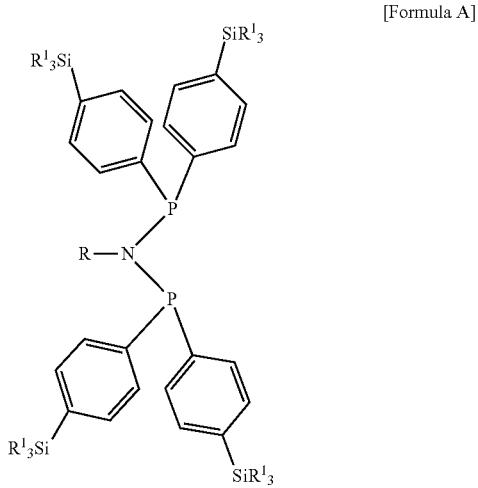

[Formula A]

In Formula A, R is a substituted or unsubstituted $C_1$ to $C_{60}$ alkyl group or a substituted or unsubstituted $C_6$ to $C_{60}$ aryl group and $R^1$s are a substituted or unsubstituted $C_1$ to $C_{60}$ alkyl group or a substituted or unsubstituted $C_6$ to $C_{60}$ aryl group.

Specifically, in Formula A, R may be $[CH_3(CH_2)_d]_2$ CH—* (d being an integer of 0 to 20). According to this embodiment, when applied to a catalyst system for ethylene oligomerization reaction, the bisphosphine ligand compound represented by Formula A can realize high activity while further improving solubility in an aliphatic hydrocarbon solvent, polymerization reaction, and uniformity of reaction products.

The bisphosphine ligand compound represented by Formula A may include a silyl group (*—Si—$(R^1)_3$) substituted with three $R^1$ groups at a phosphine terminal to achieve remarkable improvement in activity when applied to the catalyst system for ethylene oligomerization reaction. In this case, for example, the bisphosphine ligand compound can improve activity without using expensive co-catalysts, such as methylaluminoxane (MAO) and modified-methylaluminoxane (MMAO). Accordingly, the bisphosphine ligand compound represented by Formula A can ensure compatibility between high activity and economic feasibility, thereby providing an ethylene oligomerization catalyst system more suitable for mass production and an ethylene oligomer preparation method using the same. Further, the bisphosphine ligand compound represented by Formula A suppresses generation of high molecular weight byproducts and is suitable for stable operation of a process.

In Formula A, the silyl group (*—Si—$(R^1)_3$) substituted with three $R^1$ groups may be bonded to the para-site of the benzene ring (—$C_6H_4$—) of the bisphosphine ligand. In this embodiment, when applied to the catalyst system for ethylene oligomerization reaction, the bisphosphine ligand compound represented by Formula A can remarkably improve activity while further suppressing generation of 1-hexene, thereby further improving selectivity for 1-octene, as compared with compounds in which the silyl group (*—Si—$(R^1)_3$) substituted with three $R^1$ groups is bonded to the ortho-site or the meta-site of the benzene ring.

In the silyl group (*—Si—$(R^1)_3$) substituted with three $R^1$ groups, the three $R^1$ groups may each be independent and may have the same or different alkyl groups.

In one embodiment, in Formula A, the silyl group (*—Si—$(R^1)_3$) substituted with three $R^1$ groups may have a total of 4 to 50 carbon atoms. In the chromium compound represented by Formula 1, when the silyl group (*—Si—$(R^1)_3$) substituted with three $R^1$ groups is a methyl silyl group (for example, *—$SiMe_3$) having less than 4 carbon atoms, for example, 3 carbon atoms, the chromium compound cannot realize high activity by failing to prevent conversion into a compound which has two ligands coordinated therewith and exhibiting no activity due to insufficient steric hindrance.

Specifically, in Formula A, $R^1$s are a substituted or unsubstituted $C_1$ to $C_{60}$ alkyl group or a substituted or unsubstituted $C_6$ to $C_{60}$ aryl group, in which the kind of substituent is not particularly limited. Each $R^1$ may have a linear structure, a branched structure, a ring structure, and/or the like.

More specifically, in Formula A, $R^1$s are each independently an alkyl group selected from the group of a methyl group, an ethyl group, a propyl group, an isopropyl group, a butyl group, an isobutyl group, a pentyl group, an isopentyl group, a neopentyl group, a hexyl group, a heptyl group, an octyl group, a nonyl group, and combinations thereof. In this embodiment, the bisphosphine ligand of Formula A can have a further improved effect in restriction of rotation of moieties adjacent to the P—N bond in the molecular structure.

For example, in Formula A, $R^1$s may be each independently an ethyl group, an isopropyl group, or an n-butyl group. In this example, when applied to a catalyst system for ethylene oligomerization reaction, the bisphosphine ligand compound represented by Formula A can remarkability improve activity while suppressing generation of high molecular weight byproducts to be suitable for commercial processes.

The bisphosphine ligand compound represented by Formula A may be prepared by any method known in the art without limitation.

Specifically, the bisphosphine ligand compound represented by Formula A may be prepared by reacting an amine compound including an R group with a phosphine compound including the silyl group (*—Si—$(R^1)_3$) substituted with three $R^1$ groups. In this case, the amine compound may impart the R group to the compound of Formula A and the phosphine compound may impart the silyl group (*—Si—

($R^1$)$_3$) substituted with three $R^1$ groups to the compound of Formula A. Alternatively, the bisphosphine ligand compound represented by Formula A may be prepared by reacting other organic compounds capable of imparting the R group to the compound of Formula A with a phosphine compound including the silyl group (*—Si—($R^1$)$_3$) substituted with three $R^1$ groups.

More specifically, the bisphosphine ligand compound represented by Formula A may be prepared by reacting R—NH$_2$, which is the amine compound having the R group, with X—P(—C$_6$H$_4$-p-Si—($R^1$)$_3$)$_2$, which is the phosphine compound including the silyl group (*—Si—($R^1$)$_3$) substituted with three $R^1$ groups.

In one embodiment, the bisphosphine ligand compound represented by Formula A in which R is [CH$_3$(CH$_2$)$_d$]$_2$CH—* (d being an integer of 0 to 20) may be easily prepared by reacting ([CH$_3$(CH$_2$)$_d$]$_2$CH—NH$_2$) as the amine compound with (($R^1$)$_3$—Si—C$_6$H$_4$)$_2$P—Cl as the phosphine compound. Here, [CH$_3$(CH$_2$)$_d$]$_2$CH—NH$_2$ can be easily obtained and has good economic feasibility to ensure higher availability in commercial processes.

<Chromium Compound>

Another embodiment of the present invention relates to a chromium (III) compound having a novel structure composed of non-coordinated anions and trivalent chromium cations, and is represented by Formula 1.

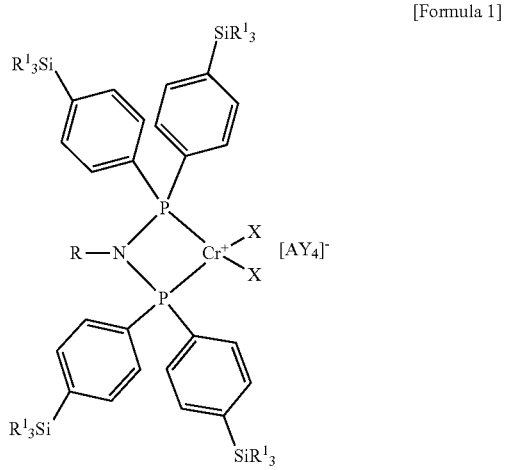

[Formula 1]

In Formula 1, R is a substituted or unsubstituted C$_1$ to C$_{60}$ alkyl group or a substituted or unsubstituted C$_6$ to C$_{60}$ aryl group; $R^1$s are a substituted or unsubstituted C$_1$ to C$_{60}$ alkyl group or a substituted or unsubstituted C$_6$ to C$_{60}$ aryl group; Xs are each independently a halogen atom, a C$_2$ to C$_{30}$ carboxylate, acetylacetonate, or a C$_1$ to C$_{30}$ hydrocarbyl group containing or free from at least one selected from among an ether group and an amine group; A is boron or aluminum; and Y is a fluorine-substituted C$_6$ to C$_{20}$ aryl group, a fluorine-substituted C$_6$ to C$_{20}$ aryloxy group, or a fluorine-substituted C$_1$ to C$_{20}$ alkoxy group.

Since chromium (III) compounds generally has a 6-coordination geometry, the chromium (III) compound of Formula 1 be additionally coordinated with ether, sulfide, amine, nitrile, H$_2$O, and/or the like, or may be present in the form of a μ2-Cl binuclear compound in which a Cl ligand contained in the chromium (III) compound of Formula 1 is shared by two chromium atoms or aluminum atoms to form a bridge.

The ether, sulfide, amine, nitrile, and H$_2$O ligands additionally coordinated to the compound of Formula 1 are removed through de-coordination upon activation by bringing an organic aluminum compound represented by Formula 2 into contact with the compound of Formula 1 when applied to the ethylene oligomerization catalyst system, and the C$_1$ ligand forming the bridge is converted into an alkyl group by the organic aluminum compound represented by Formula 2, thereby providing insignificant negative influence on realization of ethylene oligomerization catalytic reaction.

FIG. 1 shows a structure of one example of a chromium compound of Formula 1 (Compound of Formula 1-4 [(iPrN[P(C$_6$H$_4$-p-Si(iPr)Et$_2$]$_2$)-CrCl$_2$]$^+$[B(C$_6$F$_5$)$_4$]$^-$ prepared in Example 5), as analyzed by X-ray crystallography. Referring to FIG. 1, it can be seen that the chromium compound of Formula 1 according to the present invention has a nitrile ligand additionally coordinated to a chromium atom and is present in the form of the μ2-Cl binuclear compound in which the Cl ligand is shared by two chromium atoms to form a bridge.

Further, the structure indicated by a rectangular box in the left upper side of FIG. 1 is a structure of an inactive compound coordinated with two bisphosphine ligands, as arbitrarily constituted based on a structure analyzed by X-ray crystallography, and shows that such a structure cannot be obtained due to collision between the ($R^1$)$_3$Si—* groups.

Accordingly, the chromium compound according to the present invention can remarkably improve activity and selectivity for ethylene oligomerization reaction to allow 1-hexene and/or 1-octene to be prepared at high yield even without using methylaluminoxane (MAO) or modified-methylaluminoxane (MMAO), when applied to ethylene oligomerization reaction.

In ethylene oligomerization reaction, the chromium compound according to the present invention may have an optimal activity temperature of 60° C. or more, specifically 70° C. or more, more specifically 80° C. to 100° C., for example, 70° C., 80° C. or 90° C. Within this range, the chromium compound according to the present invention can further improve efficiency in control of reaction heat through air cooling or water cooling to be suitable for mass production while further improving commercial benefits.

In ethylene oligomerization reaction, the chromium compound according to the present invention can remarkably suppress generation of polyethylene byproducts, as compared with the related art. As a result, the chromium compound according to the present invention can efficiently prevent the balloon effect due to accumulation of byproducts in mass production while further improving commercial benefits.

Specifically, in Formula 1, R may be a C$_1$ to C$_{30}$ alkyl group or a C$_6$ to C$_{30}$ aryl group. More specifically, in Formula 1, R may be an alkyl group represented by [CH$_3$(CH$_2$)$_d$]$_2$CH—* (d being an integer of 0 to 20). In this embodiment, the chromium compound of Formula 1 can ensure further improvement in solubility in an aliphatic hydrocarbon solvent while further improving polymerization reaction and uniformity of reaction products when applied to a catalyst system for ethylene oligomerization reaction.

In one embodiment, R of Formula 1 may be an isopropyl group ((CH$_3$)$_2$CH—*). In this case, the chromium compound of Formula 1 can be advantageously prepared using isopropyl amine, which is inexpensive, as a raw material. Furthermore, when applied to the catalyst system for ethylene oligomerization reaction, the chromium compound of Formula 1 can realize high activity and selectivity for 1-octene.

The chromium compound of Formula 1 includes an organic silyl group bonded to the para-site (-p-) of the phenyl moiety (—$C_6H_4$—) bonded to a phosphorus (P) atom. A conventional chromium compound (for example, [{iPrN(P($C_6H_5$)$_2$)$_2$}—$CrCl_2$]$^+$[$AY_4$]$^-$) composed of ligands free from an organic silyl substituent is easily converted into a compound having a 6-coordination geometry coordinated with two ligands (that is, [{iPrN(P($C_6H_5$)$_2$)$_2$}$_2$—$CrCl_2$]$^+$ [$AY_4$]$^-$). The compound having the 6-coordination geometry coordinated with two ligands is known as not having catalytic activity. Conversely, in the chromium compound of Formula 1 according to the present invention, the organic silyl group bonded to the para-site of the phenyl moiety realizes steric hindrance to prevent the chromium compound of Formula 1 from being converted into the inactive compound having the 6-coordination geometry coordinated with two ligands (that is, [{R—N—[P(—$C_6H_4$-p-Si—($R^1$)$_3$)$_2$]$_2$}$_2$—$CrX_2$]$^+$[$AY_4$]$^-$), whereby the chromium compound can realize high activity. Furthermore, in the chromium compound of Formula 1, the organic silyl group has a Hammett substituent constant (σ) of −0.07, which is similar to hydrogen having a Hammett substituent constant (σ) of 0, thereby maximizing the effect of realizing high activity through steric hindrance while minimizing the effects of electrons in the phosphine ligands.

In the chromium compound of Formula 1, the organic silyl group is bonded to the para-site of the phenyl moiety bonded to a phosphorus (P) atom, thereby allowing the ligand to be strongly bonded to chromium by restricting rotation of the P—N bond in the bisphosphine ligand (R—N—(P($C_6H_4$—($R^1$)$_3$)$_2$)$_2$) coordinated to the chromium compound of Formula 1. When hydrogen (H) is provided to the para-site of the phenyl moiety in the chromium compound of Formula 1 (that is, when the chromium compound includes a ligand having an R—N—(P($C_6H_5$)$_2$)$_2$ structure) instead of the organic silyl group, this structure allows relatively easy rotation of the P—N bond. As a result, de-coordination of the ligand from chromium can occur and a catalyst system prepared using the chromium compound including the hydrogen (H)-introduced ligand (that is, R—N—(P($C_6H_5$)$_2$)$_2$) can generate a large amount of polyethylene (PE) byproducts at high temperature. Conversely, according to the present invention, the chromium compound of Formula 1 including the bisphosphine ligand having the organic silyl group has a relatively stable coordinator, thereby realizing high activity while minimizing generation of PE byproducts even at high temperature.

Specifically, in Formula 1, $R^1$'s are a substituted or unsubstituted $C_1$ to $C_{60}$ alkyl group or a substituted or unsubstituted $C_6$ to $C_{60}$ aryl group, in which the kind of substituent is not particularly limited. Further, each $R^1$ may have a linear structure, a branched structure, a ring structure, and/or the like.

More specifically, in Formula 1, $R^1$'s are each independently an alkyl group selected from among the group consisting of methyl, ethyl, propyl, isopropyl, butyl, isobutyl, pentyl, isopentyl, neopentyl, hexyl, heptyl, octyl, nonyl, and combinations thereof. In this embodiment, the chromium compound of Formula 1 can further improve the effect of restricting rotation of portions adjacent to the P—N bond in the molecular structure.

For example, in Formula 1, $R^1$'s may be each independently an ethyl group, an isopropyl group, or an n-butyl group. In this case, when applied to a catalyst system for ethylene oligomerization reaction, the chromium compound of Formula 1 can remarkably improve activity while suppressing generation of high molecular weight byproducts to be more suitable for commercial processes.

In one embodiment, in Formula 1, $R^1$'s may be a butyl group (n-butyl, nBu). In this embodiment, the chromium compound of Formula 1 can further remarkably improve activity and selectivity while further suppressing generation of polyethylene byproducts, when applied to the catalyst system for ethylene oligomerization reaction.

Specifically, in Formula 1, X may be a halogen atom, more specifically fluorine (F), chromium (Cl), bromine (Br), or iodine (I), for example, chlorine (Cl). In this case, the chromium compound represented by Formula 1 ensures further improvement in productivity in mass production and allows easy supply of raw materials.

Specifically, in Formula 1, Y may be $C_6F_5$, 3,5-($CF_3$)$_2C_6H_3$, or OC($CF_3$)$_3$. For example, [$AY_4$]$^-$ may be [B($C_6F_5$)$_4$]$^-$, [B((3,5-($CF_3$)$_2C_6H_3$)$_4$]$^-$, or [Al(OC($CF_3$)$_3$)$_4$]$^-$. In this case, the chromium compound represented by Formula 1 ensures further improvement in productivity in mass production and allows easy supply of raw materials.

In one embodiment, for the chromium compound of Formula 1, R may be an isopropyl group, $R^1$'s may be a butyl group (n-butyl), X may be Cl, and [$AY_4$]$^-$ may be [B($C_6F_5$)$_4$]$^-$. According to this embodiment, the chromium compound may be a compound represented by Formula 1-1. With this structure, the chromium compound can further improve activity and selectivity while further suppressing generation of polyethylene byproducts when applied to the catalyst system for ethylene oligomerization reaction.

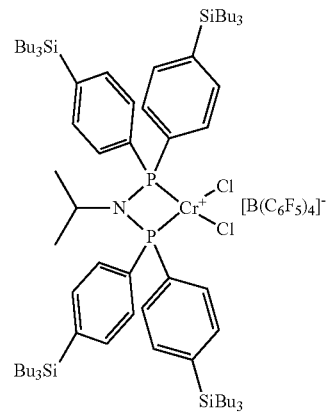

<Formula 1-1>

In another embodiment, for the chromium compound of Formula 1, R may be an isopropyl group; $R^1$'s may be each independently an isopropyl group, an ethyl group, or a butyl group; and [$AY_4$]$^-$ may be [B($C_6F_5$)$_4$]$^-$. With this structure, the chromium compound can further improve activity and selectivity while further suppressing generation of polyethylene byproducts when applied to the catalyst system for ethylene oligomerization reaction.

<Method of Preparing Chromium Compound Represented by Formula 1>

A further embodiment of the present invention relates to a method of preparing the chromium compound represented by Formula 1 described above. The chromium compound represented by Formula 1 may be prepared using the bisphosphine ligand represented by Formula A described above, thereby securing good productivity and economic feasibility.

In one embodiment, the method of preparing the chromium compound represented by Formula 1 includes: reacting an ionic compound represented by Formula I-1 with a chromium precursor compound represented by Formula Cr, followed by adding a bisphosphine ligand compound represented by Formula A to react with a reaction product of the ionic compound and the chromium precursor compound.

$$[R^4-N(H)(R^5)_2]^+[AY]^-$$ [Formula I-1]

In Formula I-1, $R^4$ is a substituted or unsubstituted $C_6$ to $C_{60}$ aryl group; $R^5$s are each independently substituted or unsubstituted $C_1$ to $C_{60}$ alkyl group; A is boron or aluminum; and Y is a fluorine-substituted $C_6$ to $C_{20}$ aryl group, a fluorine-substituted $C_6$ to $C_{20}$ aryloxy group, or a fluorine-substituted $C_1$ to $C_{20}$ alkoxy group. Details of A and Y are the same as described above.

$$Cr(X^2)_3(X^3)_m$$ [Formula Cr]

In Formula Cr, $X^2$s are each independently at least one of a halogen group, an acetylacetonate group and a carboxylate group, $X^3$s are a $C_2$ to $C_{20}$ ether-containing functional group or acetonitrile, and m is 0 or 3.

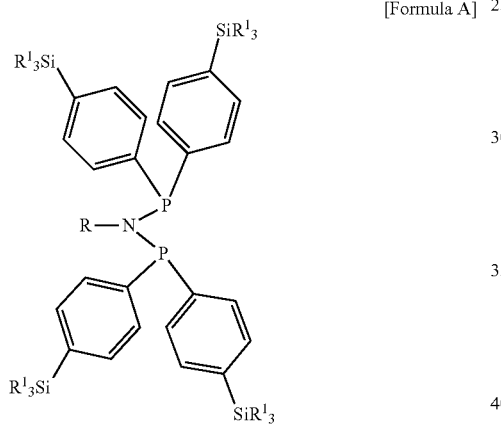

[Formula A]

In Formula A, R is a substituted or unsubstituted $C_1$ to $C_{60}$ alkyl group or a substituted or unsubstituted $C_6$ to $C_{60}$ aryl group, and $R^1$s are a substituted or unsubstituted $C_1$ to $C_{60}$ alkyl group or a substituted or unsubstituted $C_6$ to $C_{60}$ aryl group. Details of R and $R^1$ are the same as described above.

With this method, the present invention can provide a chromium compound, which can realize remarkably good reaction activity and selectivity for 1-hexene and/or 1-octene in ethylene oligomerization reaction.

In one embodiment, the $C_2$ to $C_{20}$ ether-containing functional group may include tetrahydrofuran.

Reacting the ionic compound represented by Formula I-1 with the chromium precursor compound represented by Formula Cr may include, for example, dispersing or dissolving each of the ionic compound represented by Formula I-1 and the chromium precursor compound represented by Formula Cr in a solvent, followed by mixing the resulting compounds to react with each other. Here, reaction may be performed at a temperature of room temperature (20° C.) to 100° C., specifically 20° C. to 50° C., more specifically 20° C., for 1 hour to 24 hours, specifically 1 hour to 12 hours, more specifically 12 hours, without being limited thereto.

Adding the bisphosphine ligand compound represented by Formula A may include, for example, adding the bisphosphine ligand compound dispersed or dissolved in a solvent to the reaction product of the ionic compound of Formula I-1 and the chromium precursor compound of Formula Cr to react therewith. Here, reaction may be performed at a temperature of room temperature (20° C.) to 100° C., specifically 20° C. to 50° C., more specifically 20° C., for 10 minutes to 5 hours, specifically 10 minutes to 3 hours, more specifically 2 hours, without being limited thereto.

The solvent may be selected from any solvents without limitation so long as the solvent does not obstruct reaction between the components while exhibiting good dispersion or solubility. Specifically, the solvent may be acetonitrile ($CH_3CN$), dichloromethane ($CH_2Cl_2$), and/or the like.

In one embodiment, reaction for preparation of the chromium compound of Formula 1 may be represented by Reaction Formula 1.

[Reaction Formula 1]

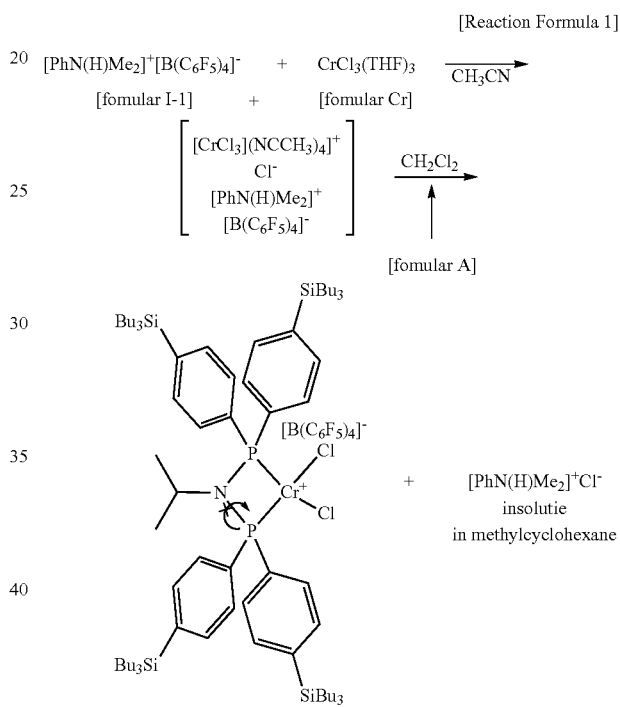

Reaction Formula 1 shows reaction by way of example when the compound of Formula I-1 is $[PhN(H)Me_2]^+[B(C_6F_5)_4]^-$, the compound of Formula Cr is $CrCl_3(THF)_3$, and the compound of Formula A is $iPrN[P(C_6H_4\text{-}p\text{-}Si(nBu)_3)_2]_2$.

In this example of Reaction Formula 1, $[PhN(H)Me_2]^+[B(C_6F_5)_4]^-$ and $CrCl_3(THF)_3$ are separately dissolved in acetonitrile ($CH_3CN$), and mixed with each other, followed by stirring the resulting mixture at room temperature for about 12 hours to 30 hours. Then, after evaporation of the solvent from the resulting mixture and dissolution of the resulting mixture in dichloromethane ($CH_2Cl_2$), iPrN[P($C_6H_4$-p-Si(nBu)$_3$)$_2$]$_2$ dissolved in dichloromethane ($CH_2Cl_2$) is added to the resulting mixture, followed by reaction therebetween at room temperature for about 1 hour to 5 hours, thereby preparing a chromium compound represented by $[(iPrN[P(C_6H_4\text{-}p\text{-}Si(nBu)_3)_2]_2)\text{-}CrCl_2]^+[B(C_6F_5)_4]^-$.

In this example of Reaction Formula 1, the final chromium compound represented by $[(iPrN[P(C_6H_4\text{-}p\text{-}Si(nBu)_3)_2]_2)\text{-}CrCl_2]^+[B(C_6F_5)_4]^-$ can be dissolved in a solvent such as methyl cyclohexane, whereas $[PhN(H)Me_2]^+$

[Cl]⁻ obtained as a byproduct is insoluble in methyl cyclohexane, thereby providing merits in separation and purification.

In another embodiment, the method of preparing the chromium compound represented by Formula 1 includes: reacting an ionic compound represented by Formula I-Cr with the bisphosphine ligand compound represented by Formula A.

[CrCl$_2$(NCCH$_3$)$_4$]$^+$[AY]$^-$     [Formula I-Cr]

In Formula I-Cr, A is boron or aluminum; Y is a fluorine-substituted $C_6$ to $C_{20}$ aryl group, a fluorine-substituted $C_6$ to $C_{20}$ aryloxy group, or a fluorine-substituted $C_1$ to $C_{20}$ alkoxy group. Details of A and Y are the same as described above.

With this method, the present invention can provide a chromium compound, which can realize remarkably good reaction activity and selectivity for 1-hexene and/or 1-octene in ethylene oligomerization reaction.

Reacting the ionic compound represented by Formula I-Cr with the bisphosphine ligand compound represented by Formula A may include, for example, dispersing or dissolving each of the ionic compound of Formula I-Cr and the bisphosphine ligand compound of Formula A in a solvent, followed by mixing the resulting compounds to react with each other. Here, reaction may be performed at a temperature of room temperature (20° C.) to 50° C., specifically 20° C. to 30° C., more specifically 20° C., for 10 minutes to 5 hours, specifically 30 minutes to 3 hours, more specifically 2 hours to 3 hours, without being limited thereto.

The solvent may be selected from any solvents without limitation so long as the solvent does not obstruct reaction between the components while exhibiting good dispersion or solubility. Specifically, the solvent may be dichrolomethane (CH$_2$Cl$_2$).

In this embodiment, reaction for preparation of the chromium compound of Formula 1 may be represented by Reaction Formula 2.

[Reaction Formula 2]

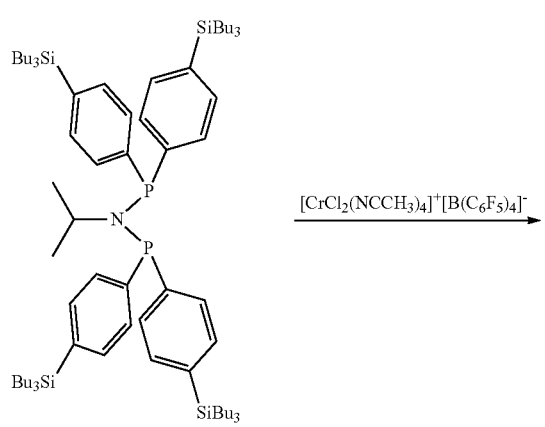

[CrCl$_2$(NCCH$_3$)$_4$]$^+$[B(C$_6$F$_5$)$_4$]$^-$

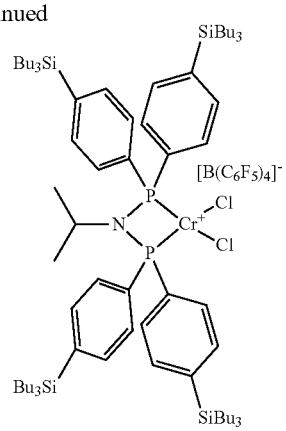

Reaction Formula 2 shows reaction by way of example when the compound of Formula I-Cr is [CrCl$_2$(NCCH$_3$)$_4$]$^+$[B(C$_6$F$_5$)$_4$]$^-$ and the compound of Formula A is iPrN[P(C$_6$H$_4$-p-Si(nBu)$_3$)$_2$]$_2$. In this example of Reaction Formula 2, [CrCl$_2$(NCCH$_3$)$_4$]$^+$[B(C$_6$F$_5$)$_4$]$^-$ and iPrN[P(C$_6$H$_4$-p-Si(nBu)$_3$)$_2$]$_2$ are separately dissolved in dichloromethane (CH$_2$Cl$_2$), and mixed with each other, followed by stirring the resulting mixture at room temperature for about 2 hours to 3 hours, thereby preparing a chromium compound represented by [(iPrN[P(C$_6$H$_4$-p-Si(nBu)$_3$)$_2$]$_2$)-CrCl$_2$][B(C$_6$F$_5$)$_4$]$^-$.

<Ethylene Oligomerization Catalyst System>

A further embodiment of the present invention relates to an ethylene oligomerization catalyst system including: the chromium compound represented by Formula 1 as a main catalyst; and an organic aluminum compound represented by Formula 2 as a co-catalyst. The catalyst system is very useful in reaction for selective conversion into 1-hexene and 1-octene. In addition, such a catalyst system is suitable for mass production and can ensure compatibility between high activity and excellent economic feasibility by remarkably improving activity and selectivity for ethylene oligomerization reaction to allow 1-hexene and/or 1-octene to be prepared at high yield even without using methylaluminoxane (MAO) or modified-methylaluminoxane (MMAO).

In the ethylene oligomerization catalyst system according to the present invention, the chromium compound represented by Formula 1 is the same as described above and detailed description thereof will be omitted herein.

(R$^2$)$_3$Al     [Formula 2]

In Formula 2, R$^2$ is a $C_1$ to $C_{20}$ alkyl group.

Specifically, in Formula 2, R$^2$s may be a methyl group, an ethyl group, an n-propyl group, an isopropyl group, an n-butyl group, an isobutyl group, or a pentyl group, and more specifically an ethyl group, or an isobutyl group.

The catalyst system according to the present invention is very useful in that the catalyst system can realize high activity while using the compound represented by Formula 2 where R$^2$s are an ethyl group or an isobutyl group. The compound represented by Formula 2 where R$^2$s are an ethyl group or an isobutyl group includes triethyl aluminum or triisobutyl aluminum, which is produced and used in mass production at low cost in the industry. Accordingly, the catalyst system according to the present invention can realize high activity and selectivity for 1-hexene and 1-octene using the compound represented by Formula 2, which can be produced at low cost and allows easy supply of raw materials, even without using expensive modified-methylaluminoxane (MMAO).

Specifically, in the catalyst system, the chromium compound represented by Formula 1 and the organic aluminum compound represented by Formula 2 may be present in a mole ratio (Cr:Al) of 1:50 to 1:500. Within this range, the catalyst system can have further improved activity.

Specifically, the catalyst system may further include a halogen-substituted or unsubstituted hydrocarbon solvent. With this solvent, the catalyst system may be present in the form of a homogeneous solution in which the reaction product is uniformly dissolved in the solvent.

More specifically, the halogen-substituted or unsubstituted hydrocarbon solvent may include, for example, toluene, xylene, chlorobenzene, dichlorobenzene, dichloromethane, methylcyclohexene, cyclohexene, hexane, and/or the like. In the exemplified solvent, the catalyst system according to the present invention can be easily formed and has more advantageous properties for separation of the solvent from 1-hexene and 1-octene, which are reaction products after oligomerization.

<Ethylene Oligomer Preparation Method>

Yet another embodiment of the present invention relates to an ethylene oligomer preparation method, which includes: selectively preparing 1-hexene and 1-octene by bringing the catalyst system including the chromium compound represented by Formula 1 and the organic aluminum compound represented by Formula 2 as a co-catalyst into contact with an ethylene monomer.

Since the ethylene oligomerization catalyst system according to the present invention may be present not only in the form of a homogeneous solution, but also in the form of being supported on a carrier, in the form of insoluble particles of a carrier, and/or the like, the ethylene oligomer preparation method (ethylene oligomerization reaction) may be a liquid phase or slurry phase reaction.

In the ethylene oligomer preparation method, reaction conditions may be modified in various ways depending upon the phase of a catalyst composition (homogeneous phase or inhomogeneous phase (carrier type)) and a polymerization method (solution polymerization, slurry polymerization). Modification of the reaction conditions can be easily carried out by those skilled in the art.

Specifically, when the ethylene oligomerization reaction (polymerization) is carried out in a liquid phase or in a slurry phase, the halogen-substituted or unsubstituted hydrocarbon solvent may be used as a medium.

More specifically, the hydrocarbon solvent may include a $C_4$ to $C_{20}$ aliphatic hydrocarbon solvent, a $C_6$ to $C_{20}$ aromatic hydrocarbon solvent, and mixtures thereof. For example, the halogen-substituted or unsubstituted hydrocarbon solvent may include toluene, xylene, chlorobenzene, dichlorobenzene, dichloromethane, methylcyclohexene, cyclohexene, hexane, and/or the like. In the exemplified solvent, the catalyst system can ensure high polymerization activity and allows easy separation of the solvent from 1-hexene and 1-octene, which are reaction products after oligomerization.

In the ethylene oligomer preparation method, although the amount of the catalyst system is not particularly limited, the catalyst system according to the present invention can realize high activity, thereby realizing good yield even when the reaction is carried out with a small amount of the catalyst system.

In one embodiment, when ethylene oligomerization reaction is carried out by a solution polymerization method, the catalyst system may be added to have a mole density (in term of chromium) of 0.001 mmol/L to 0.02 mmol/L, for example, 0.05 mmol/L to 0.015 mmol/L, followed by continuously adding an ethylene monomer to the catalyst system for reaction for 10 minutes to 1 hour, thereby preparing 1-hexene and 1-octene. The ethylene monomer may be continuously added under a pressure of 15 bar to 80 bar, specifically 40 bar to 60 bar, for example, 45 bar.

In addition, the ethylene oligomerization reaction may be carried out at a temperature of room temperature (20° C.) to 110° C., for example, 60° C. to 90° C.

Further, in the ethylene oligomerization reaction, an optimal activity temperature may be 60° C. or more, specifically 70° C. to 100° C., for example, 80° C. to 90° C. Under this condition, the ethylene oligomer preparation method can further improve efficiency in reaction heat control through air cooling or water cooling, thereby ensuring excellent applicability to mass production processes while further improving commercial advantages.

Further, the ethylene oligomerization reaction may be carried out in a batch type, in a semi-continuous type, or in a continuous type.

MODE FOR INVENTION

Example

Next, the present invention will be described in more detail with reference to some examples. It should be understood that these examples are provided for illustration only and are not to be in any way construed as limiting the present invention.

Details of components used in Examples and Comparative Examples are as in (1) to (4).

(1) An ionic compound represented by $[PhN(H)Me_2]^+[B(C_6F_5)_4]^-$ was prepared from TCI.

(2) A compound represented by $[CrCl_2(NCCH_3)_4]^+[B(C_6F_5)_4]^-$ was prepared based on a method disclosed in a document (Non-patent Document 6: ACS Omega 2017, 2, 765-773).

(3) A compound represented by $ClP[C_6H_4\text{-}p\text{-}Si(R^1)_{3\text{-}n}(R^2)_n]_2$ was prepared based on a method disclosed in a document (Non-patent Document 7: Angewandte Chemie International Edition 2016, 55, 12351).

[Reaction Formula A]

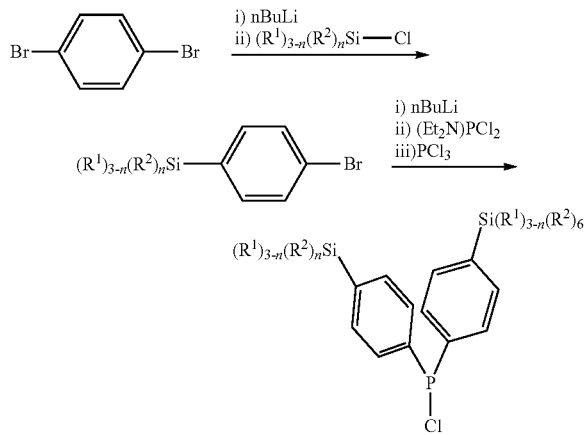

(4) A compound represented by [(CH$_3$)(CH$_2$)$_{16}$]$_2$C(H)N(PPh$_2$)$_2$ was prepared based on a method disclosed in a document (Non-patent Document 6: ACS Omega 2017, 2, 765-773).

Preparative Example 1

A solution obtained by dissolving iPrNH$_2$ (0.174 g, 2.94 mmol) in CH$_2$Cl$_2$ (10 mL) was added dropwise to a CH$_2$Cl$_2$ (30 mL) solution containing ClP[C$_6$H$_4$-p-Si(nBu)$_3$]$_2$ (3.64 g, 5.89 mmol) and Et$_3$N (2.98 g, 29.4 mmol). The resulting solution was left for a day (overnight) while stirring the resulting solution at room temperature, followed by removing a volatile component from the resulting compound through a vacuum line. After treatment of the remaining material with hexane (40 mL), an insoluble byproduct ((Et$_3$NH)$^+$Cl$^-$) was removed therefrom through Celite-aided filtration. The filtered solution was passed through a short pad of silica gel pretreated with hexane/Et$_3$N (v/v, 50:1).

Through the above process, a colorless oil compound (2.72 g, 70%) free from the solvent was prepared. NMR spectrum analysis showed that the prepared compound had a level of purity not requiring additional purification. It was confirmed that the prepared compound had a structure represented by Formula C1.

iPrN[P(C$_6$H$_4$-p-Si(nBu)$_3$)$_2$]$_2$ [Formula C1]

$^1$H NMR (600 MHz, C$_6$D$_6$): δ 8.10-7.27 (br, 8H), 7.50 (d, J=7.2 Hz, 8H), 3.86 (m, NCH, 1H), 1.42-1.33 (br, 48H), 1.24 (d, J=7.2 Hz, NCHCH$_3$, 6H), 0.92 (t, J=6.6 Hz, CH$_3$, 36H), 0.87-0.82 (br, SiCH$_2$, 24H) ppm. $^{13}$C{$^1$H} NMR (150 MHz, C$_6$D$_6$): δ 12.58 (nBu), 14.05 (nBu), 14.37, 23.07, 24.51 (t, J$_{P-C}$=7.2 Hz), 26.54 (nBu), 27.22 (nBu), 31.99, 132.4-133.0 (br), 134.2 (d, J$_{P-C}$=5.7 Hz), 138.83 ppm. $^{31}$P (243 MHz, C$_6$D$_6$): δ 42.17, 54.96 ppm. HRMS (FAB): m/z calcd (M$^+$ C$_{75}$H$_{131}$NP$_2$Si$_4$) 1219.8834, found 1219.8829.

Preparative Example 2

A compound was prepared in the same manner as in Preparative Example 1 except that ClP[C$_6$H$_4$-p-Si(iPr)$_3$]$_2$ (1.00 g, 1.88 mmol) was used instead of ClP[C$_6$H$_4$-p-Si(nBu)$_3$]$_2$.

As prepared through the above process, a compound (0.160 g, 19%) had a level of purity analyzable through recrystallization in toluene at −30° C. It was confirmed that the prepared compound had a structure represented by Formula C2.

iPrN[P(C$_6$H$_4$-p-Si(iPr)$_3$)$_2$]$_2$ [Formula C2]

$^1$H NMR (600 MHz, C$_6$D$_6$): δ 8.12-7.26 (br, 8H), 7.45 (d, J=6.6 Hz, 8H), 3.83 (m, NCH, 1H), 1.32 (m, SiCH, 12H), 1.23 (d, J=6.6 Hz, NCHCH$_3$, 6H), 1.10 (t, J=7.8 Hz, CH$_3$, 72H) ppm. $^{13}$C{$^1$H} NMR (150 MHz, C$_6$D$_6$): δ 11.10, 18.83, 21.44, 24.41 (t, J$_{P-C}$=5.7 Hz), 132.1-132.9 (br), 135.33 (d, J$_{P-C}$=5.7 Hz), 135.49-135.65 (br) ppm. $^{31}$P (243 MHz, C$_6$D$_6$): δ 43.63, 54.34 ppm.

Preparative Example 3

A compound was prepared in the same manner as in Preparative Example 1 except that ClP[C$_6$H$_4$-p-SiEt$_3$]$_2$ (1.00 g, 2.23 mmol) was used instead of ClP[C$_6$H$_4$-p-Si(nBu)$_3$]$_2$.

Through the above process, a colorless viscous oil compound (0.428 g, 50%) was prepared. It was confirmed that the prepared compound had a structure represented by Formula C3.

iPrN[P(C$_6$H$_4$-p-SiEt$_3$)$_2$]$_2$ [Formula C3]

$^1$H NMR (600 MHz, C$_6$D$_6$): 8.16-7.20 (br, 8H), 7.44 (d, J=6.6 Hz, 8H), 3.87 (m, NCH, 1H), 1.32 (m, SiCH, 12H), 1.27 (d, J=6.0 Hz, NCHCH$_3$, 6H), 0.98 (t, J=7.8 Hz, CH$_3$, 36H), 0.74 (q, J=7.2 Hz, SiCH$_2$, 24H) ppm. $^{13}$C{$^1$H} NMR (150 MHz, C$_6$D$_6$): δ 3.70, 7.72, 24.58 (t, J$_{P-C}$=5.7 Hz), 133.1-132.5 (br), 134.32, 137.97, 141.02-141.58 (br) ppm. $^{31}$P (243 MHz, C$_6$D$_6$): δ 43.01, 54.90 ppm.

Preparative Example 4

A compound was prepared in the same manner as in Preparative Example 1 except that ClP[C$_6$H$_4$-p-Si(iPr)Et$_2$] (1.58 g, 3.30 mmol) was used instead of ClP[C$_6$H$_4$-p-Si(nBu)$_3$]$_2$.

Through the above process, a white glassy solid compound (1.02 g, 68%) was prepared. It was confirmed that the prepared compound had a structure represented by Formula C4.

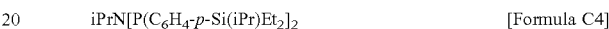
iPrN[P(C$_6$H$_4$-p-Si(iPr)Et$_2$]$_2$ [Formula C4]

$^1$H NMR (600 MHz, C$_6$D$_6$): 8.05-7.24 (br, 8H), 7.44 (d, J=7.2 Hz, 8H), 3.85 (m, NCH, 1H), 1.25 (d, J=6.6 Hz, NCHCH$_3$, 6H), 1.06-0.95 (br, 52H), 0.80 (q, J=7.2 Hz, SiCH$_2$, 24H) ppm. $^{13}$C{$^1$H} NMR (150 MHz, C$_6$D$_6$): δ 2.28, 7.89, 12.12, 18.19, 24.53 (t, J$_{P-C}$=5.7 Hz), 52.70 (t, J$_{P-C}$=10.1 Hz), 132.22-133.09 (br), 134.70 (d, J$_{P-C}$=5.7 Hz), 137.07 ppm. $^{31}$P (243 MHz, C$_6$D$_6$): δ 43.18, 54.62 ppm.

Preparative Example 5

A compound was prepared in the same manner as in Preparative Example 1 except that ClP[C$_6$H$_4$-p-Si(iPr)Me$_2$]$_2$ (0.56 g, 1.3 mmol) was used instead of ClP[C$_6$H$_4$-p-Si(nBu)$_3$]$_2$.

Through the above process, a white glassy solid compound (0.25 g, 45%) was prepared. It was confirmed that the prepared compound had a structure represented by Formula C5.

iPrN[P(C$_6$H$_4$-p-Si(iPr)Me$_2$]$_2$ [Formula C5]

$^1$H NMR (600 MHz, C$_6$D$_6$): 8.09-7.20 (br, 8H), 7.44 (d, J=6.0 Hz, 8H), 3.90 (m, NCH, 1H), 1.29 (d, J=6. Hz, NCHCH$_3$, 6H), 0.97 (d, J=6.0 Hz, 24H), 0.89 (m, SiCH, 4H), 0.19 (d, J=4.8 Hz, SiCH$_3$, 24H) ppm. $^{13}$C{$^1$H} NMR (150 MHz, C$_6$D$_6$): δ −5.2, 14.09, 17.84, 24.64 (t, J$_{P-C}$=5.7 Hz), 132.41-132.89 (br), 134.07 (d, J$_{P-C}$=5.9 Hz), 139.17 ppm. $^{31}$P (243 MHz, C$_6$D$_6$): δ 43.43, 54.23 ppm.

Preparative Example 6

A compound was prepared in the same manner as in Preparative Example 1 except that ClP[C$_6$H$_4$-p-Si(1-octyl)Me$_2$]$_2$ (1.82 g, 3.24 mmol) was used instead of ClP[C$_6$H$_4$-p-Si(nBu)$_3$]$_2$.

Through the above process, a colorless viscous oil compound (1.22 g, 68%) was prepared. It was confirmed that the prepared compound had a structure represented by Formula C6.

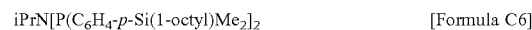
iPrN[P(C$_6$H$_4$-p-Si(1-octyl)Me$_2$]$_2$ [Formula C6]

$^1$H NMR (600 MHz, C$_6$D$_6$): 8.14-7.22 (br, 8H), 7.48 (d, J=6.6 Hz, 8H), 3.92 (m, NCH, 1H), 1.41-1.19 (br, 48H), 1.31 (d, J=6.6 Hz, NCHCH$_3$, 6H), 0.92 (t, J=7.2 Hz, CH$_3$, 12H), 0.78-0.72 (br, SiCH$_2$, 8H), 0.25 (d, J=1.8 Hz, SiCH$_3$, 24H) ppm. $^{13}$C{$^1$H} NMR (150 MHz, C$_6$D$_6$): δ −2.82, 14.41, 16.07, 23.14, 24.38, 24.69, 29.8 (d, $J_{P-C}$=5.7 Hz), 32.39, 34.10, 132.8 (d, $J_{P-C}$=21.45 Hz), 133.73 (d, $J_{P-C}$=5.7 Hz), 140.32 ppm. $^{31}$P (243 MHz, $C_6D_6$): δ 42.90, 54.96 ppm.

Preparative Example 7

A compound was prepared in the same manner as in Preparative Example 1 except that $ClP[C_6H_4$-p-SiMe$_3]_2$ (1.54 g, 4.23 mmol) was used instead of $ClP[C_6H_4$-p-Si(nBu)$_3]_2$.

Through the above process, a colorless viscous oil compound (0.564 g, 37%) was prepared. It was confirmed that the prepared compound had a structure represented by Formula C7.

[Formula C7]

$^1$H NMR (600 MHz, $C_6D_6$): 7.93-7.32 (br, 8H), 7.43 (d, J=7.2 Hz, 8H), 3.94 (m, NCH, 1H), 1.33 (d, J=6.6 Hz, NCHCH$_3$, 6H), 0.20 (s, J=7.2 Hz, SiCH$_3$, 36H) ppm. $^{13}$C{$^1$H} NMR (150 MHz, $C_6D_6$): δ −1.10, 23.15, 24.76 (t, $J_{P-C}$=5.7 Hz), 26.66, 26.82, 33.02, 35.71, 52.52 (t, $J_{P-C}$=10.1 Hz), 132.80 (d, $J_{P-C}$=20.1 Hz), 133.50 (d, $J_{P-C}$=4.2 Hz), 140.98 ppm. $^{31}$P (243 MHz, $C_6D_6$): δ 43.40, 54.62 ppm.

Example 1

A chromium compound having a structure represented by Formula 1-1 was prepared by the following method.

[Formula 1-1]

A solution obtained by dissolving $[PhN(H)Me_2]^+[B(C_6F_5)_4]^-$ (0.15 g, 0.23 mmol) in acetonitrile (2.9 mL) was added to a solution obtained by dissolving $CrCl_3(THF)_3$ (0.085 g, 0.23 mmol) in acetonitrile (2.9 mL). The resulting solution was left for a day (overnight) while stirring the resulting solution at 25° C., followed by removing a volatile component from the resulting solution through a vacuum line. A solution was obtained by dissolving the obtained green remaining compound in $CH_2Cl_2$ (2.0 mL) and a solution obtained by dissolving iPrN[P($C_6H_4$-p-Si(nBu)$_3$)$_2$]$_2$ (0.28 g, 0.23 mmol) prepared in Preparative Example 1 in $CH_2Cl_2$ (4.6 mL) was added dropwise to the obtained solution. As a result, the obtained solution was immediately changed from a green color to a bluish-green color. Then, after stirring the solution at 25° C. for 2 hours, the solvent was removed from the solution through a vacuum line. After treatment of the remaining material with methyl cyclohexane, an insoluble material was removed therefrom through Celite-aided filtration. As a result, a bluish-green viscous oil compound (0.46 g, 99% based on the formula of $[(iPrN[P(C_6H_4$-p-Si(nBu)$_3)_2]_2)$-$CrCl_2][B(C_6F_5)_4]^-)$ free from the solvent was prepared.

An insoluble material (white solid mixed with a small amount of green solid, separated solid) was obtained from the top of the Celite filter using $CH_2Cl_2$.

After removal of the solvent from the remaining product, signals corresponding to N,N-dimethylaniline units were confirmed through 1H NMR spectrum analysis. The weight of the separated solid (41 mg) was roughly coincident with a theoretically expected weight (36 mg) of byproducts ($[PhN(H)Me_2]^+Cl^-$). The separated solid was dissolved in $CH_3CN$ (1.0 mL) and was treated with a solution obtained by dissolving $AgNO_3$ (78 mg, 0.46 mmol) in $CH_3CN$ (1.0 mL). White solid precipitates (38 mg) were generated in an amount roughly corresponding to a theoretically expected weight (33 mg) of AgCl.

FIG. 2 shows $^{31}$P NMR spectrum, $^1$H NMR spectrum, $^{19}$F NMR spectrum and EPR spectrum analysis results of the chromium compound prepared in Example 1.

Example 2

A chromium compound having a structure represented by Formula 1-1 was prepared by the following method.

[Formula 1-1]

A solution obtained by dissolving iPrN[P($C_6H_4$-p-Si(nBu)$_3$)$_2$]$_2$ (0.10 g, 0.082 mmol) prepared in Preparative Example 1 in $CH_2Cl_2$ (1.8 mL) was added dropwise to a solution obtained by dissolving $[CrCl_2(NCCH_3)_4]^+$ $[B(C_6F_5)_4]^-$ (0.079 g, 0.082 mmol) in $CH_2Cl_2$ (0.5 mL).

The resulting solution was stirred at room temperature for 2.5 hours, followed by removing the solvent from the resulting solution through a vacuum line, thereby preparing a bright green viscous oil compound (0.16 mg, 99% based on Formula: $[(iPrN[P(C_6H_4$-p-Si(nBu)$_3)_2]_2)$-$CrCl_2]^+[B(C_6F_5)_4]^-)$.

It was confirmed that $^{31}$P NMR spectrum, $^1$H NMR spectrum, $^{19}$F NMR spectrum and EPR spectrum analysis results of the chromium compound prepared in Example 2 were substantially identical to those of the spectrum analysis results (FIG. 2) of the chromium compound prepared in Example 1.

Example 3

A chromium compound having a structure represented by Formula 1-2 was prepared in the same manner as in Example 2 except that the bisphosphine ligand prepared in Preparative Example 2 was used instead of the bisphosphine ligand prepared in Preparative Example 1. A dark green solid compound (0.086 g, 98%) was prepared.

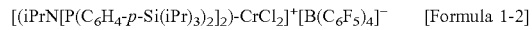

[Formula 1-2]

Example 4

A chromium compound having a structure represented by Formula 1-3 was prepared in the same manner as in Example 2 except that the bisphosphine ligand prepared in Preparative Example 3 was used instead of the bisphosphine ligand prepared in Preparative Example 1. A dark green solid compound (0.052 g, 98%) was prepared.

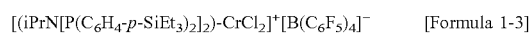

[Formula 1-3]

Example 5

A chromium compound having a structure represented by Formula 1-4 was prepared in the same manner as in Example 2 except that the bisphosphine ligand prepared in Preparative Example 4 was used instead of the bisphosphine ligand prepared in Preparative Example 1. A dark green solid compound (0.092 g, 99%) was prepared.

[Formula 1-4]

FIG. 1 shows a structure of the chromium compound prepared in Example 5, as analyzed by X-ray crystallography.

Example 6

A chromium compound having a structure represented by Formula 1-5 was prepared in the same manner as in Example 2 except that the bisphosphine ligand prepared in Preparative Example 5 was used instead of the bisphosphine ligand prepared in Preparative Example 1. A dark green solid compound (0.096 g, 98%) was prepared.

[(iPrN[P(C$_6$H$_4$-$p$-Si(iPr)Me$_2$]$_2$)-CrCl$_2$]$^+$[B(C$_6$F$_5$)$_4$]$^-$ [Formula 1-5]

Example 7

A chromium compound having a structure represented by Formula 1-6 was prepared in the same manner as in Example 2 except that the bisphosphine ligand prepared in Preparative Example 6 was used instead of the bisphosphine ligand prepared in Preparative Example 1. A green viscous oil compound (0.084 g, 98%) was prepared.

[(iPrN[P(C$_6$H$_4$-$p$-Si(1-octyl)Me$_2$]$_2$)-CrCl$_2$]$^+$ [B(C$_6$F$_5$)$_4$]$^-$ [Formula 1-6]

Comparative Example 1

A chromium compound having a structure represented by Formula 1-7 was prepared in the same manner as in Example 2 except that the bisphosphine ligand prepared in Preparative Example 7 and having a —SiMe$_3$ substituent exhibiting insignificant steric hindrance was used instead of the bisphosphine ligand prepared in Preparative Example 1. A dark green solid compound (0.103 g, 97%)) was prepared.

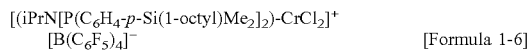
[(iPrN[P(C$_6$H$_4$-$p$-SiMe$_3$)$_2$]$_2$)-CrCl$_2$]$^+$[B(C$_6$F$_5$)$_4$]$^-$ [Formula 1-7]

Comparative Example 2

A chromium compound having a structure represented by Formula 1-8 was prepared using iPrN[P(C$_6$H$_5$)$_2$]$_2$ and [CrCl$_2$(NCCH$_3$)$_4$]$^+$[B(C$_6$F$_5$)$_4$]$^-$ by a method disclosed in a document (Non-patent Document 6: ACS Omega, 2017, 2, 765-773).

[(iPrN[P(C$_6$H$_5$)$_2$]$_2$)—CrCl$_2$]$^+$[B(C$_6$F$_5$)$_4$]$^-$ [Formula 1-8]

Comparative Example 3

A chromium compound having a structure represented by Formula 1-9 was prepared using [CH$_3$(CH$_2$)$_{16}$]$_2$CHN[P(C$_6$H$_5$)$_2$]$_2$ and [CrCl$_2$(NCCH$_3$)$_4$]$^+$[B(C$_6$F$_5$)$_4$]$^-$ by a method disclosed in a document (Non-patent Document 6: ACS Omega, 2017, 2, 765-773).

{[CH$_3$(CH$_2$)$_{16}$]$_2$CHN[P(C$_6$H$_5$)$_2$]$_2$)—CrCl$_2$}$^+$ [B(C$_6$F$_5$)$_4$]$^-$ [Formula 1-9]

Example 8

ETHYLENE OLIGOMERIZATION REACTION

In a dried reactor (75 mL bomb reactor) inside a glove box, methyl cyclohexane (19 mL) and the chromium compound (0.41 mg, 0.20 µmol) of Formula 1-1 prepared in Example 1 were placed. After assembling the reactor, the reactor was taken out of the glove box. iBu$_3$Al (15.9 mg, 0.080 mmol) was dissolved in methyl cyclohexane (1 mL) and was injected into the reactor at room temperature through a syringe, followed by immediate injection of ethylene gas into the reactor under a pressure of 45 bar. The temperature of the reactor was spontaneously increased from 20° C. to 90° C. for 3.5 minutes through by exothermic reaction. When the temperature of the reactor reached 90° C., a fan was operated to remove heat therefrom. The temperature of the reactor was additionally increased to 96° C. for 5 minutes and was slowly reduced to 88° C. for 25 minutes. After ethylene oligomerization reaction was carried out for 25 minutes, the reactor was dipped in an ice-containing water tank for cooling and the ethylene gas was discharged from the reactor to complete the reaction.

For gas chromatography analysis (GC analysis) of the generated substance, nonane (0.700 g) was added to the final reaction product according to an internal standard. After measurement of the content of each of generated oligomers (1-octene (1-C8), 1-hexene (1-C6), methylcyclopentane+methylenecyclopentane (cy-C6), and higher oligomers above C10 (>C10)) through gas chromatography analysis (GC analysis), the content of each of the generated oligomers was converted into a percentage based on the weight thereof. Generated polyethylene (PE) having a solid phase was separated at 80° C. through filtration to measure the weight of the separated PE byproducts, followed by calculating wt % of PE based on Equation: [weight of generated PE (g)/weight of ethylene used in reaction (g)].

Example 9

Ethylene Oligomerization Reaction

Ethylene oligomerization reaction was carried out by the same method as in Example 8 except that the chromium compound of Formula 1-1 prepared in Example 2 was used instead of the chromium compound of Formula 1-1 prepared in Example 1, the reaction temperature was adjusted to a temperature of 24° C. to 98° C., and the reaction time was adjusted to 30 minutes.

Example 10

Ethylene Oligomerization Reaction

Ethylene oligomerization reaction was carried out by the same method as in Example 9 except that the reaction temperature was adjusted to a temperature of 28° C. to 75° C., and the reaction time was adjusted to 30 minutes.

Example 11

Ethylene Oligomerization Reaction

Ethylene oligomerization reaction was carried out by the same method as in Example 9 except that the reaction temperature was adjusted to a temperature of 26° C. to 60° C. and the reaction time was adjusted to 30 minutes.

Example 12

Ethylene Oligomerization Reaction

Ethylene oligomerization reaction was carried out by the same method as in Example 8 except that the chromium compound of Formula 1-2 was used instead of the chromium compound of Formula 1-1, the reaction temperature was adjusted to a temperature of 25° C. to 84° C., and the reaction time was adjusted to 30 minutes.

Example 13

Ethylene Oligomerization Reaction

Ethylene oligomerization reaction was carried out by the same method as in Example 8 except that the chromium compound of Formula 1-3 was used instead of the chromium compound of Formula 1-1, the reaction temperature was adjusted to a temperature of 25° C. to 85° C., and the reaction time was adjusted to 30 minutes.

Example 14

Ethylene Oligomerization Reaction

Ethylene oligomerization reaction was carried out by the same method as in Example 8 except that the chromium compound of Formula 1-4 was used instead of the chromium compound of Formula 1-1, the reaction temperature was adjusted to a temperature of 22° C. to 89° C., and the reaction time was adjusted to 30 minutes.

Example 15

Ethylene Oligomerization Reaction

Ethylene oligomerization reaction was carried out by the same method as in Example 8 except that the chromium compound of Formula 1-5 was used instead of the chromium compound of Formula 1-1, the reaction temperature was adjusted to a temperature of 25° C. to 79° C., and the reaction time was adjusted to 30 minutes.

Example 16

Ethylene Oligomerization Reaction

Ethylene oligomerization reaction was carried out by the same method as in Example 8 except that the chromium compound of Formula 1-6 was used instead of the chromium compound of Formula 1-1, the reaction temperature was adjusted to a temperature of 24° C. to 82° C., and the reaction time was adjusted to 30 minutes.

Comparative Example 4

Ethylene Oligomerization Reaction

Ethylene oligomerization reaction was carried out by the same method as in Example 8 except that the chromium compound of Formula 1-7 was used instead of the chromium compound of Formula 1-1, the reaction temperature was adjusted to a temperature of 25° C. to 35° C. and the reaction time was adjusted to 35 minutes.

Comparative Example 5

Ethylene Oligomerization Reaction

Ethylene oligomerization reaction was carried out by the same method as in Example 8 except that the chromium compound of Formula 1-8 was used instead of the chromium compound of Formula 1-1, the reaction temperature was adjusted to 45° C., and the reaction time was adjusted to 30 minutes.

Comparative Example 6

Ethylene Oligomerization Reaction

Ethylene oligomerization reaction was carried out by the same method as in Example 8 except that the chromium compound of Formula 1-9 was used instead of the chromium compound of Formula 1-1, the reaction temperature was adjusted to 45° C., and the reaction time was adjusted to 30 minutes.

Activity of olefin polymerization reaction of Examples 8 to 16 and Comparative Examples 4 to 6 and the compositions of prepared olefins are shown in Table 1.

TABLE 1

| | Chromium compound | Temp (° C.); time (min) | Activity (Kg/g-Cr/h) | 1-C8 (wt %) | 1-C6 (wt %) | cy-C6 (wt %) | >C10 (wt %) | PE (wt %) |
|---|---|---|---|---|---|---|---|---|
| Example 8 | Formula 1-1 | 20~96; 25 | 4700 | 45.4 | 32.4 | 3.0 | 19.0 | 0.01 |
| Example 9 | Formula 1-1 | 24~98; 15 | 6310 | 45.1 | 34.5 | 3.0 | 17.2 | 0.03 |
| Example 10 | Formula 1-1 | 28~75; 30 | 4420 | 52.8 | 25.7 | 3.6 | 17.8 | 0.03 |
| Example 11 | Formula 1-1 | 26~60; 30 | 3640 | 67.0 | 15.9 | 3.4 | 13.4 | 0.03 |
| Example 12 | Formula 1-2 | 25~84; 30 | 3020 | 55.8 | 27.2 | 3.2 | 13.7 | 0.05 |
| Example 13 | Formula 1-3 | 25~85; 30 | 2760 | 58.1 | 25.6 | 3.3 | 12.7 | 0.18 |
| Example 14 | Formula 1-4 | 22~89; 30 | 3260 | 53.8 | 28.6 | 3.1 | 14.3 | 0.02 |
| Example 15 | Formula 1-5 | 25~79; 30 | 2430 | 63.0 | 21.8 | 3.8 | 11.15 | 0.01 |
| Example 16 | Formula 1-6 | 24~82; 30 | 2890 | 55.5 | 25.3 | 3.5 | 15.5 | 0.06 |
| Comparative Example 4 | Formula 1-7 | 25~35 | 0 | — | — | — | — | — |
| Comparative Example 5 | Formula 1-8 | 45; 30 | 26 | 68.0 | 10.5 | 4.5 | 14.9 | 1.3 |
| Comparative Example 6 | Formula 1-9 | 45; 30 | 84 | 70.3 | 14.3 | 4.7 | 9.4 | 1.0 |

As could be seen from the experimental results shown in Table 1, when the chromium compounds of Formulas 1-1 to 1-6 according to the present invention having $C_4$ to $C_{50}$ silyl group (*—Si($R^1$)$_3$) substituents exhibiting significant steric hindrance at the para-site thereof were applied to a catalyst system for ethylene oligomerization reaction, the catalyst system exhibited excellent activities in the range of 2400 kg/g-Cr/h to 6300 kg/g-Cr/h. Conversely, it could be seen that, in ethylene oligomerization reaction of Comparative Examples 4 to 6 using the chromium compound of Formula 1-7 having a $C_3$ organic silyl group (*—SiMe$_3$) exhibiting insufficient steric hindrance and the chromium compounds of Formulas 1-8 and 1-9 free from the *—Si($R^1$)$_3$ substituent, the catalyst systems had much lower reaction activities (1/30 to 1/250) than the catalyst systems of Examples 8 to 16.

In particular, it could be seen that, since the catalyst system for ethylene oligomerization reaction including the chromium compound of Formula 1-1 according to the present invention having the *—Si(nBu)$_3$ substituent exhibiting significant steric hindrance had a very high maximum activity of 6300 kg/g-Cr/h, generated a very small amount of polyethylene (PE) byproducts (0.01 wt %), and acted as a catalyst without any problem at a high temperature of about 90° C., the chromium compound of Formula 1-1 was suitable for commercial processes.

It should be understood that various modifications, changes, alterations, and equivalent embodiments can be made by those skilled in the art without departing from the spirit and scope of the invention.

The invention claimed is:

1. A bisphosphine ligand compound represented by Formula A:

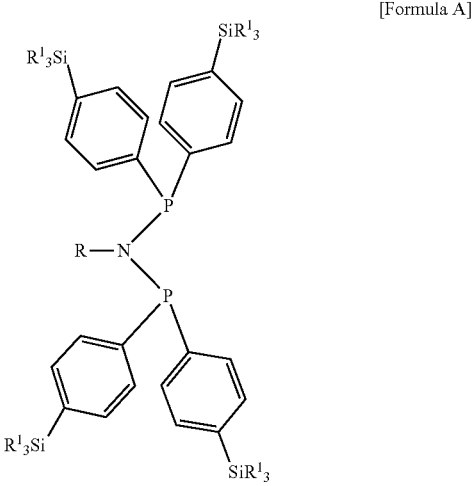

[Formula A]

wherein Formula A, R is a substituted or unsubstituted $C_1$ to $C_{60}$ alkyl group or a substituted or unsubstituted $C_6$ to $C_{60}$ aryl group and $R^1$s are a substituted or unsubstituted $C_1$ to $C_{60}$ alkyl group or a substituted or unsubstituted $C_6$ to $C_{60}$ aryl group.

2. The bisphosphine ligand compound according to claim 1, wherein, in Formula A, R is $[CH_3(CH_2)_d]_2CH-$* (d being an integer of 0 to 20) and $R^1$s are each independently an ethyl group, an isopropyl group, or an n-butyl group.

3. A chromium compound represented by Formula 1:

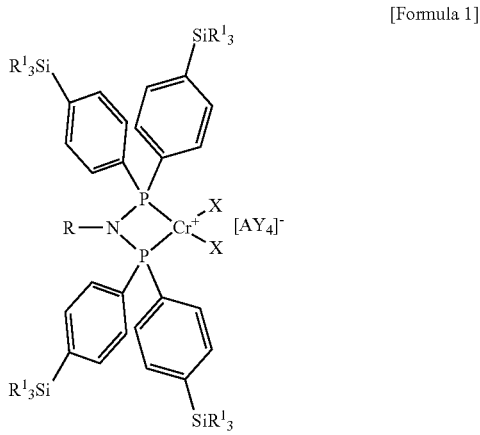

[Formula 1]

wherein Formula 1, R is a substituted or unsubstituted $C_1$ to $C_{60}$ alkyl group or a substituted or unsubstituted $C_6$ to $C_{60}$ aryl group; $R^1$s are a substituted or unsubstituted $C_1$ to $C_{60}$ alkyl group or a substituted or unsubstituted $C_6$ to $C_{60}$ aryl group; Xs are each independently a halogen atom, a $C_2$ to $C_{30}$ carboxylate, acetylacetonate, or a $C_1$ to $C_{30}$ hydrocarbyl group containing or free from at least one selected from among an ether group and an amine group; A is boron or aluminum; and Y is a fluorine-substituted $C_6$ to $C_{20}$ aryl group, a fluorine-substituted $C_6$ to $C_{20}$ aryloxy group, or a fluorine-substituted $C_1$ to $C_{20}$ alkoxy group.

4. The chromium compound according to claim 3, wherein, in Formula 1, $[AY_4]^-$ is $[B(C_6F_5)_4]^-$.

5. The chromium compound according to claim 3, wherein, in Formula 1, R is $[CH_3(CH_2)_d]_2CH-$*(d being an integer of 0 to 20) and $R^1$s are each independently an ethyl group, an isopropyl group, or an n-butyl group.

6. The chromium compound according to claim 3, wherein, in Formula 1, R is an isopropyl group; $R^1$s are an n-butyl group; Xs are Cl; and $[AY_4]^-$ is $[B(C_6F_5)_4]^-$.

7. An ethylene oligomerization catalyst system comprising:
a chromium compound represented by Formula 1; and
an organic aluminum compound represented by Formula 2;

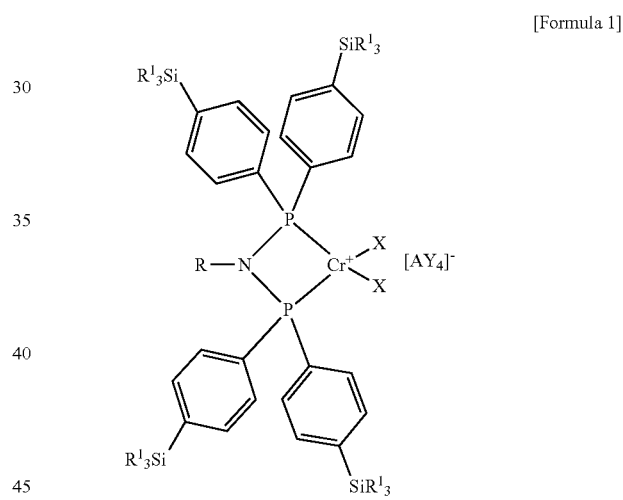

[Formula 1]

wherein Formula 1, R is a substituted or unsubstituted $C_1$ to $C_{60}$ alkyl group or a substituted or unsubstituted $C_6$ to $C_{60}$ aryl group; $R^1$s are a substituted or unsubstituted $C_1$ to $C_{60}$ alkyl group or a substituted or unsubstituted $C_6$ to $C_{60}$ aryl group; Xs are each independently a halogen atom, a $C_2$ to $C_{30}$ carboxylate, acetylacetonate, or a $C_1$ to $C_{30}$ hydrocarbyl group containing or free from at least one selected from among an ether group and an amine group; A is boron or aluminum; and Y is a fluorine-substituted $C_6$ to $C_{20}$ aryl group, a fluorine-substituted $C_6$ to $C_{20}$ aryloxy group, or a fluorine-substituted $C_1$ to $C_{20}$ alkoxy group;

$(R^2)_3Al$       [Formula 2]

wherein Formula 2, $R^2$ is a $C_1$ to $C_{20}$ alkyl group.

8. The ethylene oligomerization catalyst system according to claim 7, wherein, in Formula 2, $R^2$ is an isobutyl group or an ethyl group.

9. The ethylene oligomerization catalyst system according to claim 7, wherein, in Formula 1, R is an isopropyl group;

and $R^1$s are each independently an ethyl group, an isopropyl group, or an n-butyl group; Xs are Cl; and $[AY_4]^-$ is $[B(C_6F_5)_4]^-$.

10. An ethylene oligomer preparation method, comprising: selectively preparing at least one of 1-hexene and 1-octene by bringing the catalyst system according to claim 7 into contact with an ethylene monomer.

* * * * *